US005603694A

United States Patent [19]
Brown et al.

[11] Patent Number: 5,603,694
[45] Date of Patent: Feb. 18, 1997

[54] INFUSION COIL APPARATUS AND METHOD FOR DELIVERING FLUID-BASED AGENTS INTRAVASCULARLY

[76] Inventors: Joe E. Brown, 1900 Glenn Club Dr., #1106, Stone Mountain, Ga. 30087; Matt D. Pursley, 430 Cameron Woods Ct., Alpharetta, Ga. 30202

[21] Appl. No.: 602,424

[22] Filed: Feb. 16, 1996

[51] Int. Cl.$^6$ ..................................................... A61M 31/00
[52] U.S. Cl. ............................................. 604/49; 604/281
[58] Field of Search ................................. 604/49, 51, 52, 604/53, 280, 281, 264; 128/656–658; 623/1

[56] References Cited

U.S. PATENT DOCUMENTS

| | | | |
|---|---|---|---|
| 4,531,933 | 7/1985 | Norton et al. | 604/281 X |
| 4,694,838 | 9/1987 | Wijayarthna et al. | 604/281 X |
| 5,163,928 | 11/1992 | Hobbs et al. | 604/281 |
| 5,383,928 | 1/1995 | Scott et al. | 623/1 |

Primary Examiner—John D. Yasko
Attorney, Agent, or Firm—Ronald P. Kananen; Jeffrey L. Thompson

[57] ABSTRACT

An infusion coil apparatus and method for delivering fluid-based diagnostic and therapeutic agents intravascularly in which an infusion coil is placed in an artery or other vessel at a diseased location, and then fluid-based agents are delivered through the infusion coil to that specific location. The infusion coil apparatus includes a resilient fiber core enclosed in a soft, hollow polymer tubing. The resilient fiber core has a preshaped coil at one end that overcomes the susceptibility of the infusion coil to become uncoiled, while permitting a construction of the infusion coil having a very small diameter. The polymer tubing is radiopaque and has a soft surface for engaging the inside of a vessel. The infusion coil is deployed by a deployment device at a specific site in a vessel to be treated. Once at the delivery site, the deployment device ejects the infusion coil out of a delivery sheath into the vessel. The infusion coil is perforated so that fluid-based agents can be delivered through the infusion coil to the site adjacent the wall of the vessel. Variations in the shape of the coil and in the deployment devices are disclosed.

52 Claims, 8 Drawing Sheets

FIG. 4
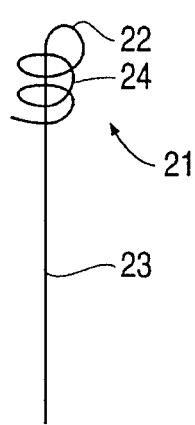
FIG. 5
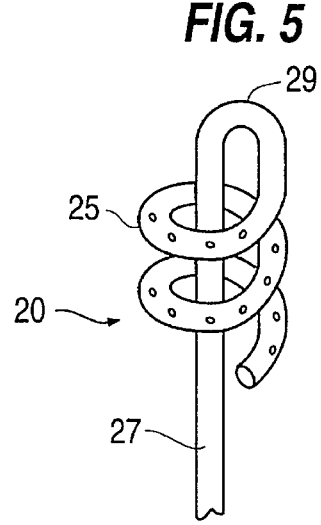
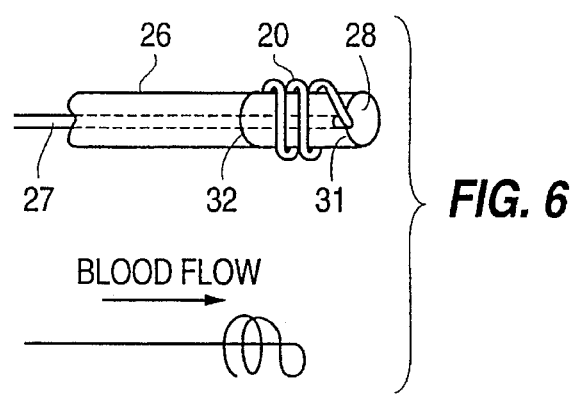
BLOOD FLOW
FIG. 6
FIG. 7
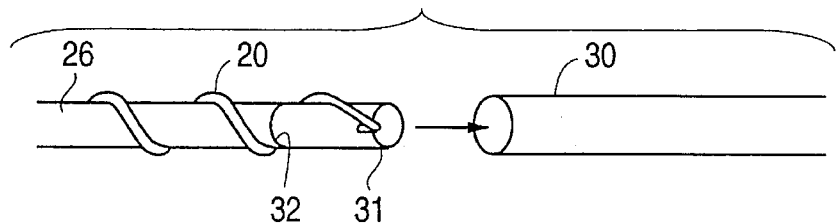
FIG. 8
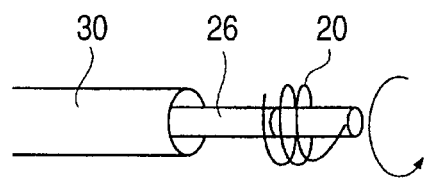

INFUSION COIL APPARATUS AND METHOD FOR DELIVERING FLUID-BASED AGENTS INTRAVASCULARLY

BACKGROUND OF THE INVENTION

1. Field of the Invention

The present invention relates generally to an apparatus and method for delivering fluid-based diagnostic and therapeutic agents (hereinafter referred to as "fluid-based agents") and, in particular, to an infusion coil apparatus and method for delivering such fluid-based agents intravascularly.

2. Description of the Related Art

Atherosclerosis is a cardiovascular disease in which deposits of plaques (atheromas) containing cholesterol, lipid material, foam cells, lipophages and proliferating smooth muscle cells are within the intima and media of large to small diameter arteries such as the aorta and the iliac, femoral, coronary and cerebral arteries. The resultant stenosis causes reduction in blood flow.

Attempts to treat atherosclerosis have included bypass surgery wherein the diseased vascular segments are augmented by prosthetic or natural grafts. This procedure requires general anesthesia and a substantial healing period after surgery and, thus, is generally limited to cases of severe coronary artery disease.

Other approaches for the recanalization of stenotic vessels include percutaneous transluminal coronary angioplasty (PTCA), atherectomy, stenting and newer modalities of cardiovascular intervention, including laser angioplasty. The primary drawbacks of these procedures has been the appearance of restenosis at or near the site of the original stenosis in the blood vessel that requires a secondary angioplasty procedure or a bypass surgery. Another occurrence that reduces the success of a typical angioplasty procedure is that frequently the stenotic plaque or intima of the blood vessel or both are dissected during the angioplasty procedure by the inflation of the balloon. Upon the deflation of the balloon, a section of the dissected lining (commonly termed "flap") will collapse into the bloodstream, thereby closing or significantly reducing the blood flow through the vessel. In these instances, emergency bypass surgery is often required to avoid a myocardial infarct distal to the blockage.

In recent years, various devices and methods (other than bypass surgery) for prevention of restonosis and for repairing damaged blood vessels have become known. These methods typically use an expandable cage or region (commonly termed "stent") on the distal end of a catheter designed to hold a detached lining against an arterial wall for extended periods to facilitate the reattachment thereof. Some stents are designed for permanent implantation inside the blood vessel, and others are designed for temporary use inside the vessel.

Typically, the expandable region of the prior art stents is formed by a braided wire or balloon attached to the distal end of the catheter body. Such designs are difficult and expensive to manufacture, and create reliability concerns due to the existence of high stress points located at the connection of the braided wire region with the catheter body and at the connections between the intermingled wire strands.

Alternatively, or in addition to the use of stents, various drugs have been applied to the site of the dilated lesion to prevent or reduce chances of restenosis and to aid in the healing of flaps, dissection or other hemorrhagic conditions that may appear after an angioplasty procedure. The prior art braided wire and balloon stents, as disclosed, for example, in U.S. Pat. Nos. 4,655,771, 5,295,962, 5,368,566 and 5,421,826, cannot be used to deliver or inject fluid-based agents to the specific site of the lesion while maintaining adequate flow in the vascular lumen. The fluid flow through the lumen is substantially blocked by these stents during use.

In recognition of this problem, temporary stenting catheters with drug delivery capabilities have been developed, as disclosed, for example, in U.S. Pat. Nos. 5,383,928 and 5,415,637. The '928 patent discloses a coil-shaped stent covered by a polymer sheath for local drug delivery. A drug is incorporated into the polymer sheath for controlled release of the drug upon insertion. Because the polymer sheath itself is as large as the diameter of the coil, the device cannot be removed from the subject outside of the lab and without a guiding catheter. Moreover, the device is limited in its ability to adapt to the shape and size of the vessel wall, and in that only drugs that are compatible with and can be incorporated into the polymer can be delivered by the device.

The temporary stenting catheter of the '637 patent functions to hold a collapsed dissected lining or flap against the blood vessel wall for a sufficient time to allow the natural adhesion of the flap to the blood vessel wall. The stenting catheter of the '637 patent also functions to introduce a drug to the site of the vascular procedure to aid in the adhesion process and in the prevention of restenosis while allowing the flow of blood through the vessel to locations distal to the catheter.

The catheter assembly of the '637 patent, however, has a number of disadvantages. The catheter assembly is complex and expensive to manufacture. More importantly, however, the catheter assembly of the '637 is very expensive to use because it requires a guiding catheter to be maintained within the vessel and the patient to be maintained within the catheter lab during use and deployment.

There are other known devices, as disclosed, for example, in U.S. Pat. Nos. 4,531,933, 4,694,838, 4,813,925, 4,887,996, and 5,163,928, that use a catheter having a heat set polymer stent at a distal end shaped as a halo or coil. These devices require pushing a rod through the lumen of the heat set curve in the polymer to straighten the device so that it may be inserted into the body through a guide catheter. The rod is then removed and the curve shape of the catheter comes back. These devices suffer from being limited in size due to the fact that a relatively large wire must be used to straighten the device (e.g., 0.014" to 0.016"). Thus, the lumen size of these devices are correspondingly large. The devices also suffer from a lack of ability to be deformed (i.e., coiled, bent, or shaped) without a permanent deformation. Because of the permanent deformation, the devices fail to track the inside of a vessel that is not round.

The prior art drug delivery systems cannot be left in place for a period of time outside the lab in which the angioplasty was performed, and then removed by a nurse by simply pulling the system out. Any coil that relies on a balloon for its intravascular shape requires inflation to maintain the coil's shape, and the patient is required to stay in the lab under fluoro to make sure the coil stays in place. Any coil that relies on the modules of the polymer to maintain the coil shape is too rigid to pull out and requires the use of a straightening rod to push through the coil so that the coil straightens out before removal. This procedure would not be permitted outside the catheter lab, thus, adding significant cost to the procedure.

Thus, there is a need for an improved system and method for delivering fluid-based agents intravascularly that overcomes the problems of the existing systems.

SUMMARY OF THE INVENTION

It is an object of the present invention to provide a method and system for delivering fluid-based agents intravascularly that overcomes the problems in the above-mentioned prior art.

It is a further object of the present invention to provide a delivery system for delivering fluid-based agents with an extremely soft coil shape for engaging a vessel.

It is a further object of the present invention to provide a delivery system for fluid-based agents that can be removed from the body without the use of guiding catheters or introduction devices, and that can be left in place for a period of time outside the lab where it was installed and removed by simply pulling it out.

It is a further object of the present invention to provide a delivery system for fluid-based agents that is very small and flexible, and that has an improved ability to track the inside of a vessel and to be deformed (i.e., coiled, bent, or shaped) without permanent deformation.

It is a further object of the present invention to provide a coil-shaped delivery system with the above advantages that has a radiopaque polymer tubing or radiopaque coating over a polymer tubing for observation under a fluoroscope or other X-ray device.

Additional objects, advantages, and novel features of the invention will be set forth in the following description, and will become apparent to those skilled in the art upon reading this description or practicing the invention. The objects and advantages of the invention may be realized and attained by the appended claims.

To achieve the foregoing and other objects and in accordance with the purpose of the present invention, as embodied and broadly described herein, the infusion coil apparatus of the present invention comprises a resilient fiber core having a linear portion and a coiled portion, and a polymer tubing encasing the resilient fiber core and adapting to the shape of the resilient fiber core, the polymer tubing comprising a first portion encasing the linear portion of the resilient fiber core and a second portion encasing the coiled portion of the resilient fiber core.

In a preferred embodiment, the polymer tubing has a lumen extending along a length of the polymer tubing, and the second portion of the polymer tubing comprises means for releasing a fluid-based agent delivered through the lumen from the infusion coil apparatus. The releasing means may comprises a series of openings spaced along the second portion of the polymer tubing, or a porous, braided, or stitched material of the polymer tubing.

With the construction of the present invention, the infusion coil can be extremely small. For example, the resilient fiber core can be formed of a metallic steel heat-tempered spring alloy, such as a titanium-nickel-chromium alloy, or a boron fiber having a diameter of 0.002 to 0.006 inches. The polymer tubing can have an outside diameter of 0.012 to 0.014 inches and an inside diameter of 0.006 to 0.008 inches. The polymer tubing is preferably formed of a very soft material, such as nylon, urethane, PE and TFE polymer materials, and has a Shore D hardness of approximately 40 so as to minimize resistance to the coiled portion of the resilient fiber core and prevent damage to a vessel during use. The polymer tubing is constructed of a polymer compounded with a radio opacifier at a loading high enough to make the polymer radiopaque.

In a first embodiment, the coiled portion of the resilient fiber core is shaped into a forward feed coil shape extending away from the linear portion of the resilient fiber core.

In a second embodiment, the resilient fiber core is shaped into a reverse feed coil shape with a bent transition portion between the linear portion and the coiled portion, the bent transition portion directing the coiled portion in a reverse direction back along the linear portion.

In additional embodiments, the coiled portion of the resilient fiber core is shaped into a forward feed coil shape extending away from the linear portion of the resilient fiber core and includes a distal end portion that can be engaged by a catheter for deployment purposes.

In a further aspect of the present invention, in accordance with its objects and purposes, the present invention comprises a combination of an infusion coil apparatus for delivering fluid-based agents intravascularly and an apparatus for deploying the infusion coil apparatus at a desired location in a vessel, the infusion coil apparatus comprising a resilient fiber core having a linear portion and a coiled portion, and a polymer tubing encasing the resilient fiber core and adapting to the shape of the resilient fiber core, the polymer tubing comprising a first portion encasing the linear portion of the resilient fiber core and a second portion encasing the coiled portion of the resilient fiber core.

The apparatus for deploying the infusion coil apparatus comprises a delivery sheath, the delivery sheath having an inside diameter that is smaller than a preset diameter of the coiled portion for compressing the infusion coil apparatus during deployment.

In the first embodiment, the apparatus for deploying the infusion coil apparatus further comprises a push tube for pushing the infusion coil apparatus out of the delivery sheath during deployment, the push tube being slidable over a linear portion of the infusion coil apparatus.

In the second embodiment, the apparatus for deploying the infusion coil apparatus further comprises a deployment catheter that is slidable over the infusion coil apparatus, the deployment catheter comprising a slotted distal end for receiving the bent transition portion of the infusion coil apparatus to permit pushing and twisting of the infusion coil apparatus during deployment.

In the third and fourth embodiments, the apparatus for deploying the infusion coil apparatus further comprises a deployment catheter having a means for holding the distal end portion to permit pushing and twisting of the infusion coil apparatus during deployment. In the third embodiment, the holding means comprises a notch and snare or other suitable holding structure across a distal end of the deployment catheter for receiving and holding the distal end portion of the infusion coil apparatus. In the fourth embodiment, the holding means utilizes a friction lock formed in the distal end of the deployment catheter into which the distal end portion of the infusion coil apparatus can be inserted and securely held during deployment.

In the second, third, and fourth embodiments, a first marker is preferably provided at a forward distal end of the deployment catheter and a second marker is spaced axially rearwardly from the first marker. The first and second markers are radiopaque for determining placement of the infusion coil apparatus within a vessel. The first and second markers are spaced apart a distance equal to an axial length of the coiled portion in a relaxed position of the coiled portion.

According to a fifth embodiment of the present invention, the deployment apparatus is further provided with a proximal holding tube positioned over a linear portion of the infusion coil. The proximal holding tube has a distal end abutting a coiled portion of the infusion coil and is secured to the infusion coil. The proximal holding tube permits manipulation of the infusion coil during deployment using the proximal holding tube in conjunction with the deployment catheter.

In a sixth embodiment of the present invention, the delivery sheath of the deployment apparatus further comprises a guide tube extending from a point adjacent a distal end of the delivery sheath to an opening in a side wall of the delivery sheath. The guide tube is secured to the side wall of the delivery sheath and has an inner diameter large enough to permit a guide wire to pass therethrough.

In a further aspect of the present invention, in accordance with its objects and purposes, the present invention comprises a method for delivering fluid-based agents into a vessel, comprising the steps of providing an infusion coil apparatus having a resilient fiber core encased by a soft polymer tubing, loading the infusion coil apparatus into a delivery sheath, the delivery sheath having an internal diameter which is smaller than a preset diameter of a coiled portion of the resilient fiber core, inserting the delivery sheath and the infusion coil apparatus into a vessel, and pushing the infusion coil apparatus out of the delivery sheath whereby the resilient fiber core causes the infusion coil apparatus to increase in diameter and lodge in the vessel. The method further comprises the step of feeding a fluid-based agent through the polymer tubing of the infusion coil apparatus into the vessel.

In the first embodiment of the present invention, the method further comprises the steps of sliding a push tube over a linear portion of the infusion coil apparatus, pushing the infusion coil apparatus out of the delivery sheath using the push tube, and removing the push tube and the delivery sheath from the vessel while maintaining the infusion coil apparatus within the vessel.

In the second embodiment of the present invention, the method further comprises the steps of providing the infusion coil apparatus with a reverse feed coil shape with a bent transition portion between a linear portion and a coiled portion, the bent transition portion directing the coiled portion in a reverse direction back along the linear portion, providing a deployment catheter having a slotted distal end, sliding the deployment catheter over the infusion coil apparatus and receiving the bent transition portion of the infusion coil apparatus in the slotted distal end of the deployment catheter.

In the third and fourth embodiments of the present invention, the method further comprises the steps of providing the infusion coil apparatus with a forward feed coil shape extending away from a linear portion of the resilient fiber core, and a distal end portion, providing a deployment catheter having a holding structure in a distal end of the deployment catheter, and receiving and securing the distal end portion of the infusion coil apparatus in the holding structure of the deployment catheter.

In the second, third, and fourth embodiments, the method further comprises pushing the infusion coil apparatus out of the delivery sheath into the vessel with the deployment catheter, and twisting the deployment catheter to rewind the infusion coil apparatus into a deployed position against a wall of the vessel. The method also includes providing first and second radiopaque marks on the deployment catheter, the first and second marks being spaced apart a distance approximately equal to an axial length of the coiled portion in a relaxed position of the infusion coil apparatus, and twisting the deployment catheter to rewind the infusion coil apparatus until the axial length of the coiled portion is approximately the same as the distance between the first and second marks.

In accordance with the fifth embodiment of the present invention, the method for delivering fluid-based agents further comprises the steps of providing the infusion coil apparatus with a forward feed coil shape extending away from a linear portion of the resilient fiber core, providing a proximal holding tube over a linear portion of the infusion coil, the proximal holding tube having a distal end abutting a coiled portion of the infusion coil, the proximal holding tube being secured to the infusion coil, sliding the proximal holding tube and the deployment catheter in opposite directions to elongate and reduce the diameter of a coiled portion of the infusion coil apparatus, placing the elongated coil into the delivery sheath, pushing the infusion coil apparatus out of the delivery sheath into the vessel using the deployment catheter and the proximal holding tube, and sliding the proximal holding tube and the deployment catheter in opposite directions to compress and increase the diameter of the coiled portion of the infusion coil apparatus, whereby the infusion coil apparatus is placed in a deployed position against a wall of the vessel.

In accordance with the sixth embodiment of the present invention, the method further comprises the steps of providing a guide tube within the delivery sheath, the guide tube having a first distal end adjacent to a distal end of the delivery sheath, and a second proximal end in communication with an opening through a side wall of the delivery sheath, and sliding the guide tube over a guide wire to facilitate the step of inserting the delivery sheath and the infusion coil apparatus into a vessel.

BRIEF DESCRIPTION OF THE DRAWINGS

The present invention will become more clearly appreciated as the disclosure of the present invention is made with reference to the accompanying drawings. In the drawings:

FIG. 3A shows the infusion coil in a loaded position. FIG. 3B shows the infusion coil in a deployed position within an artery wall. FIG. 3C shows the removal of the deployment mechanism.

FIG. 4 is a perspective view of a resilient fiber in an alternate coil shape according to a second embodiment of the present invention.

FIG. 5 is a perspective view of an infusion coil assembly according to the second embodiment.

FIGS. 6 to 8 illustrate the steps and mechanism for deploying the infusion coil of the second embodiment. FIG. 6 shows the infusion coil in a relaxed position on a deployment catheter. FIG. 7 shows the infusion coil in a stretched position on the deployment catheter during insertion into a guide catheter. FIG. 8 shows the torquing of the deployment catheter to rewind the infusion coil.

FIG. 13A shows the infusion coil in a shortened, radially enlarged position. FIG. 13B shows the infusion coil in an elongated, radially reduced position. FIG. 13C shows a perspective view of the infusion coil and deployment apparatus.

DETAILED DESCRIPTION OF THE PREFERRED EMBODIMENT

A first embodiment of the present invention will be described in detail hereinafter with reference to FIGS. 1, 2, and 3A to 3C.

Figure 1:
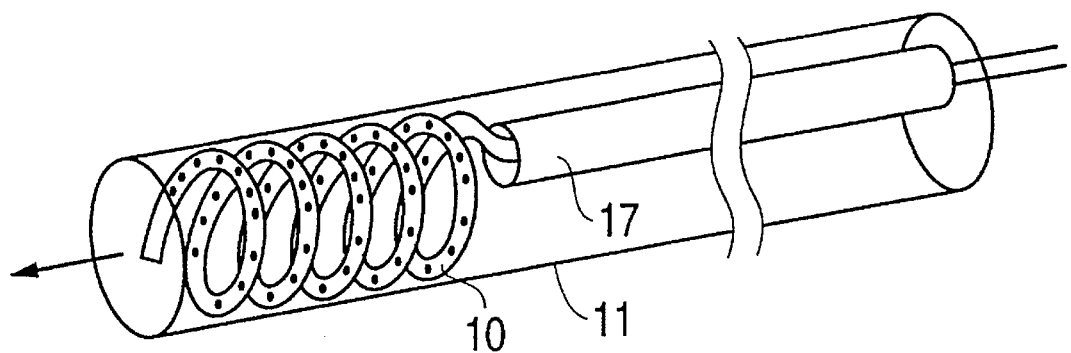
FIG. 1 is a perspective view of an infusion coil assembly according to a first embodiment of the present invention.
Figure 2:
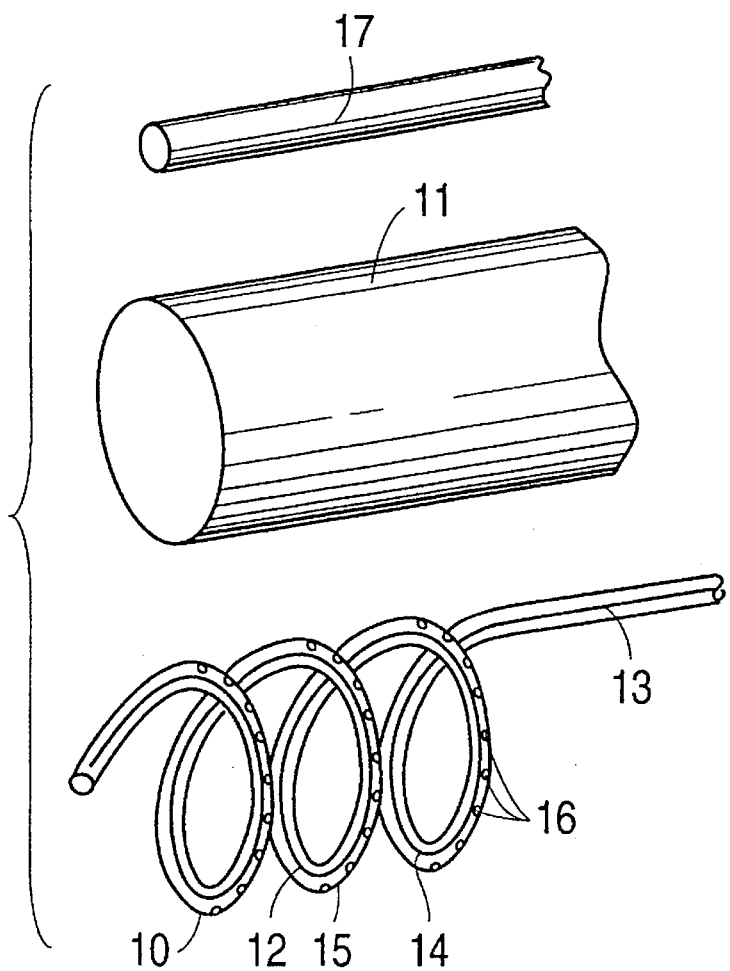
FIG. 2 is an exploded perspective view of the components shown in FIG. 1.
Figure 3A:
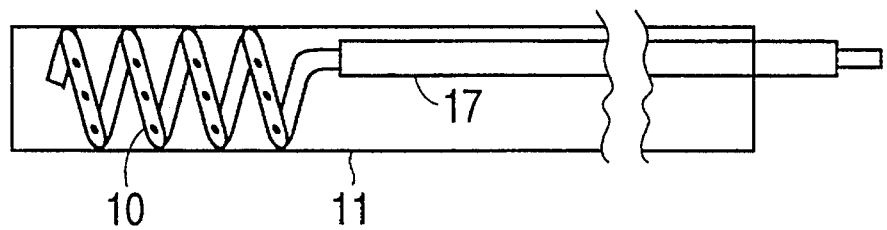
FIGS. 3A to 3C illustrate the steps and mechanism for deploying the infusion coil of the first embodiment.
Figure 3B:
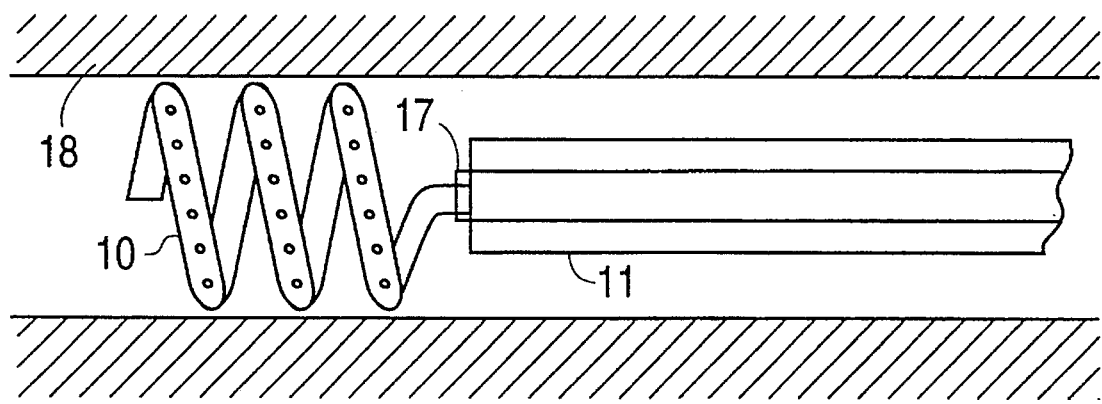
Figure 3C:
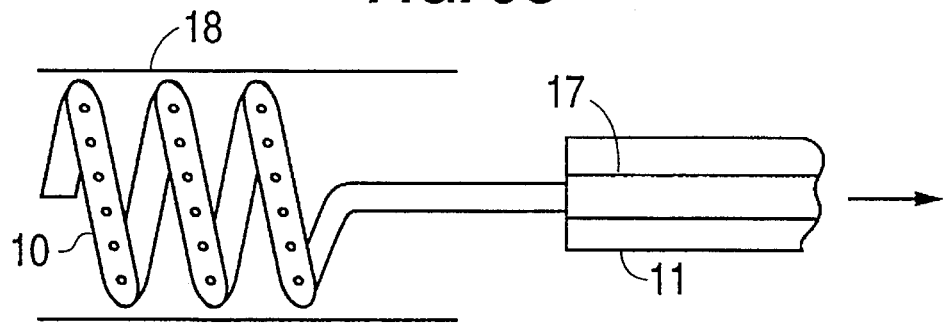

Referring to FIG. 1, an infusion coil 10 according to the first embodiment is shown in a loaded configuration (i.e., prior to deployment) in a delivery sheath 11 for deployment into a vessel of a subject. The infusion coil 10 includes a pre-shaped resilient fiber core 12, as seen in the exploded view of FIG. 2. The resilient fiber core 12 has a first linear portion 13 and a second coiled portion 14. The coiled portion 14 is formed at an end of the device for insertion into a vessel. The resilient fiber core 12 is encased by a soft, radiopaque polymer tubing 15 that adapts to the shape of the resilient fiber core 12, including the coiled portion 14. The resilient fiber core 12 extends through the lumen of the soft polymer tubing 15.

The preshape of the coiled portion 14 of the resilient fiber core 12 is a coil configuration with an outer diameter of the coil chosen so that it is slightly larger than the vessel in which the infusion coil 10 will be deployed. The combination of the resilient fiber core 12 and the soft polymer tubing 15 permit the infusion coil 10 to be wound into a much tighter coil than coils for delivering fluid-based agents of the prior art.

The soft polymer tubing 15 includes a series of holes 16 therein spaced along the circumference of the coil shape. The holes 16 provide an outlet for fluid-based agents injected through the tubing 15. The holes 16 in the tubing 15 may be formed by drilling, lasing, machining, punching, and so forth. Slots can be used in the coil of the tubing 15 instead of holes. In addition, the coiled portion of the tubing 15 can be constructed of porous materials such as PTFE and PVDF, or the end of the tubing can be braided, stitched, and so forth.

In operation, the infusion coil 10 in its loaded position (FIGS. 1 and 3A) is inserted into the body and directed to the desired site through an appropriate guiding catheter and/or guide wire. The device can be inserted directly over a guide wire already in place, as further explained below. The axial length of the device is minimized because the infusion coil 10 is in compression during deployment.

After reaching the desired location (FIG. 3B), a push tube 17 is used to push the infusion coil 10 out of the delivery sheath 11. As the infusion coil 10 exits the sheath 11, the resilient fiber core 12 springs back to its pre-set condition and lodges the infusion coil 10 in a vessel 18. The push tube 17 is fed directly over the linear portion of the infusion coil to provide positive attachment to the coil 10 for pushing and to prevent accidental over-extension of the push tube 17 into the vessel 18. After the infusion coil 10 is pushed completely out of the delivery sheath 11, the push tube 17 and delivery sheath 11 can be removed (FIG. 3C) leaving the infusion coil 10 in the vessel 18 by itself.

The polymer tubing 15 over the resilient fiber core 12 serves to cushion the impact of the infusion coil 10 onto the wall of the vessel 18 and provides a path for infusion of fluid-based diagnostic and therapeutic agents. The holes 16 placed around the entire periphery of the polymer tube 15 in the coil section permit antithrombotic fluid-based agents to be introduced over the entire circumference of the infusion coil 10 to prevent blood clotting problems associated with the deployment of similar devices.

The following dimensions and specific materials of the components of the delivery system are given by way of example only. The delivery sheath 11 can be formed of polymer (nylon) or fluorpolymer tube (teflon) having an outside diameter of 0,066" and an inside diameter of 0.058". The push tube 17 can be formed of a polymer tube (nylon) with or without a wire reinforcement. The push tube 17 can have an outside diameter of 0.032" and an inside diameter of 0.018".

The resilient fiber core 12 of the infusion coil 10 can be formed of a metallic steel heat-tempered spring alloy, such as a titanium-nickel-chromium alloy, a boron fiber, or other suitable resilient material. The resilient fiber core preferably has a diameter of 0.002" to 0.006". The polymer tubing 15 can be formed of a nylon, urethane, PE or TFE polymer material having an outside diameter of 0.012" to 0.014" and an inside diameter of 0.006" to 0.008". The polymer tubing 15 of the coil 10 is preferably very soft so that it offers virtually no resistance to the coiled portion 14 of the preformed resilient fiber core 12. This allows the resilient fiber core 12 to be as small as 0.002" diameter and still maintain enough springback in the coil assembly to be lodged into a vessel 18. This is a crucial aspect of the device in that it is soft enough to prevent damage to the walls of the vessel 18 as it is inserted and removed.

Referring to FIGS. 4 to 8, a second embodiment of the present invention will be described. In the second embodiment, an infusion coil 20 is formed using a resilient fiber core 21 that is preshaped into a reverse feed coil shape, as shown in FIG. 4. Specifically, a bent transition portion 22 between a linear portion 23 of the resilient fiber core 21 and a coiled portion 24 of the resilient fiber core 21 directs the coiled portion 24 in a reverse direction back along the linear portion 23, rather than forward away from the linear portion, as in the embodiment of FIG. 1.

A polymer tubing 25 is then slid over the resilient fiber core 21, as in the first embodiment, and the infusion coil 20 takes the shape of the resilient fiber core 21, as shown in FIG. 5.

Referring to FIGS. 6 to 8, the steps and mechanism for deploying the infusion coil 20 of the second embodiment will be described. FIG. 6 shows the infusion coil 20 in a relaxed position on a deployment catheter 26. The deployment catheter 26 is slid over a linear portion 27 of the infusion tube 20. The deployment catheter 26 includes a slotted distil end 28 for receiving a portion of the infusion coil 20 at or near the transition portion 29 to permit pushing and twisting of the infusion coil 20 during deployment.

As shown in FIG. 7, the infusion coil 20 is pushed through a standard introduction device 30 for deployment, such as a guide catheter (i.e., delivery sheath) or a guide wire. The infusion coil 20 elongates into a stretched position when inserted into these devices because the coil 20 has a much larger relaxed diameter (e.g., 2.5 mm to 6 mm) than the passage diameter of the guide catheter or other delivery devices 30 (e.g., 1.5 mm to 2.5 mm). Once at the desired deployment location, the deployment catheter 26 is pushed and twisted to force the infusion coil 20 out of the guide catheter 30 and to rewind into the coil's original configuration, as shown in FIG. 8. Since the polymer tubing 15 is radiopaque, the infusion coil 20 can be easily observed during deployment on a fluoroscope or other suitable X-ray device.

The deployment catheter includes a first marker 31 at a forward distal end and a second marker 32 spaced axially rearwardly from the first marker 31. The first and second markers 31 and 32 are radiopaque and are spaced apart a distance approximately equal to the axial length of the coil 20 in its relaxed position (FIG. 6). The markers 31 and 32 are used to determine coil placement within a vessel. Because the markers 31 and 32 are radiopaque, they can be observed using a fluoroscope or other suitable X-ray device.

Once the markers 31 and 32 are observed at the desired deployment site, the deployment catheter 26 is twisted and pushed from the guide catheter 30, as described above. The deployment catheter 26 is preferably twisted until the coil portion of the infusion coil 20 assumes an axial length approximately equal to the axial length in its relaxed position.

Figure 9:
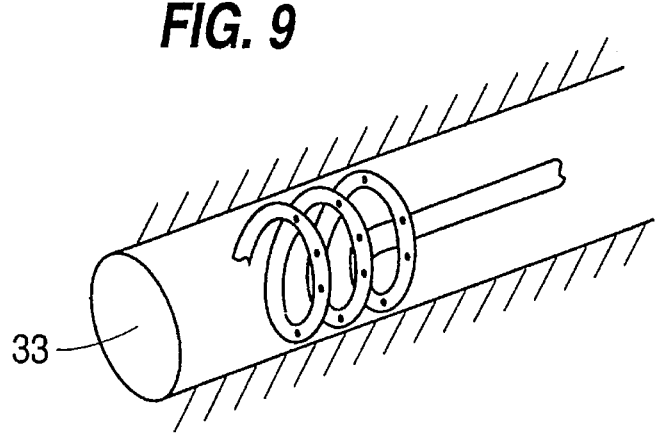
FIG. 9 is a perspective view of the infusion catheter deployed in an artery having a round cross-section.
Figure 10:
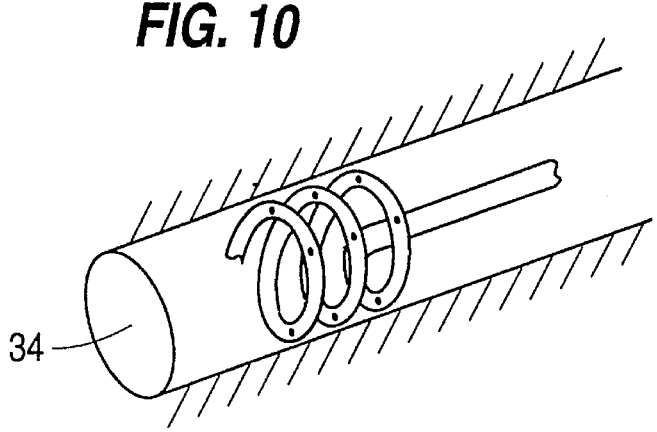
FIG. 10 is a perspective view of the infusion catheter deployed in an artery having an oval or oblong cross-section.

The deployment procedure described above for the second embodiment allows for simple positive deployment of the infusion coil 20. More importantly, the deployment procedure allows for positioning of the device in an irregularly shaped vessel while maintaining a coil configuration that is in contact with the vessel wall along its entire periphery. To illustrate this point, FIG. 9 shows the infusion coil 20 of the second embodiment deployed in an artery 33 having a round cross-section, which is an ideal deployment site for most stents and delivery devices. On the other hand, FIG. 10 shows the infusion coil 20 of the second embodiment deployed in an artery 34 having an oblong or other irregularly shaped cross-section. In both instances, the infusion coil 20 of the present invention is soft enough to conform to any differences and irregularities in the vessel wall. Moreover, the twisting motion ensures that the infusion coil 20 is placed against the vessel wall. A stiffer tube, such as one that relies on polymer resiliency to form a coil, rather than a resilient fiber core as in the present invention, will bridge such irregularities.

Figure 11:
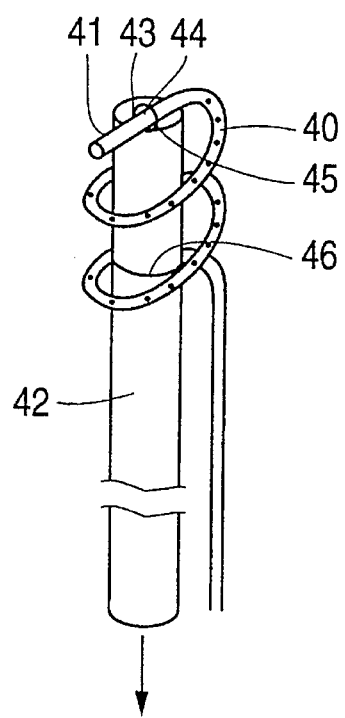
FIG. 11 is a perspective view of an infusion coil, according to a third embodiment of the present invention, in a relaxed position on a deployment catheter.

Referring to FIG. 11, a third embodiment of the present invention will be described. In the third embodiment, an infusion coil 40 with a distal end portion 41 is formed using a resilient fiber core that is preshaped into a forward-feed coil shape, as shown in FIG. 11. A deployment catheter 42 is provided for deploying the infusion coil 40 in a manner similar to that described above for the second embodiment. The deployment catheter 42 includes a notch 43 and a snare device 44 for holding the distal end portion 41 of the infusion coil 40.

With the deployment catheter 42, the distal end of the infusion coil 40 is grabbed in the snare device 44 or similar clamp at the end of the deployment catheter 42. This allows the coil 40 to be dragged into place and twisted, similar to the procedure described above for deploying the infusion coil 20 of the second embodiment. First and second markers 45 and 46 are provided to determine coil placement within a vessel, similar to the markers 31 and 32 of the second embodiment.

Figure 12A:
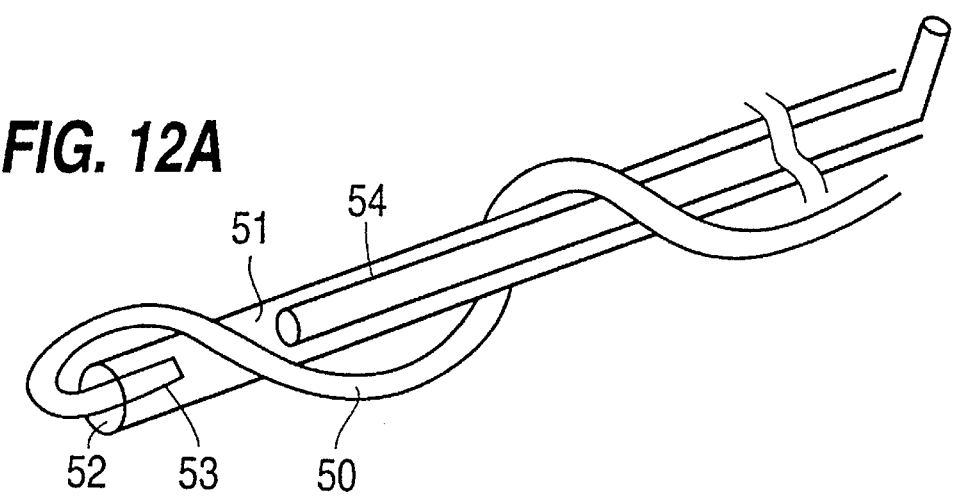
FIG. 12A is a perspective view of an infusion coil held by a friction lock of a deployment catheter according to a fourth embodiment of the present invention.
Figure 12B:
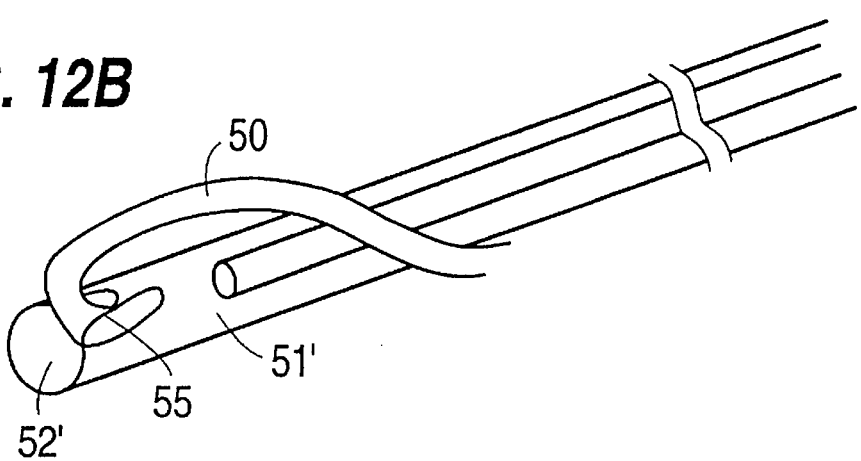
FIG. 12B is a perspective view of the deployment catheter shown in FIG. 12A with a modified friction lock.

FIGS. 12A and 12B illustrate an infusion coil apparatus according to a fourth embodiment of the present invention. As shown in FIG. 12A, the infusion coil apparatus includes an infusion coil 50 having a resilient fiber core that is preshaped into a forward-feed coil shape, as in the first and third embodiments. A deployment catheter 51 is provided for deploying the infusion coil 50 in a manner similar to that described above for the third embodiment.

The deployment catheter 51 includes a friction lock 52 formed in a distal end thereof for receiving and holding a distal end 53 of the infusion coil 50. The friction lock 52 comprises an axially extending bore at the end of the deployment catheter 51 into which the distal end 53 of the infusion coil 50 is inserted. The resilient nature of the infusion coil 50 created by the resilient fiber core creates a friction holding force between the infusion coil 50 and the axially extending bore upon insertion of the distal end 53 of the infusion coil 50 into the axially extending bore.

A push rod 54 is inserted into the deployment catheter 51 to release the friction lock 52 between the infusion coil 50 and the deployment catheter 51 after the infusion coil 50 is positioned in a vessel at a desired location. To release the friction lock 52, the push rod 54 engages and pushes the distal end 53 of the infusion coil 50 out of the axial bore of the deployment catheter 51.

As with the second and third embodiments described above, the deployment catheter 51 of the fourth embodiment, in operation, drags the infusion coil 50 into place and deploys the infusion coil 50 into a desired deployment location. The deployment catheter 51 can also be provided with radiopaque markers (not shown) to facilitate observation on a fluoroscope or other suitable X-ray device.

FIG. 12B is a perspective view of a deployment catheter 51' with a modified friction lock 52'. The modified friction lock includes a notch 55 in a side wall of the distal end of the deployment catheter 51'. In use, the infusion coil 50 is inserted into the axial bore of the deployment catheter 51' and positioned such that a distal end portion of the infusion coil 50 is received in the notch 55. The notch 55 facilitates twisting of the infusion coil 50 during deployment to rewind the infusion coil 50 into its original configuration.

Figure 13A:
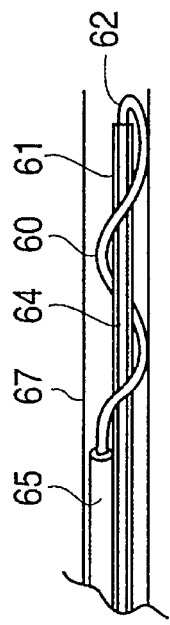
FIGS. 13A to 13C illustrate an infusion coil and deployment apparatus according to a fifth embodiment of the present invention.
Figure 13B:
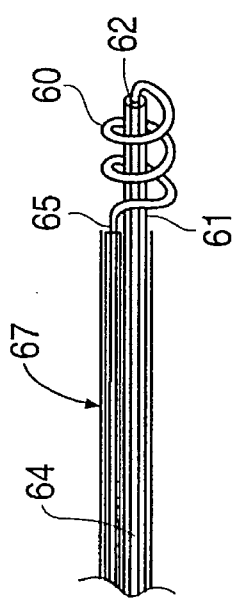
Figure 13C:
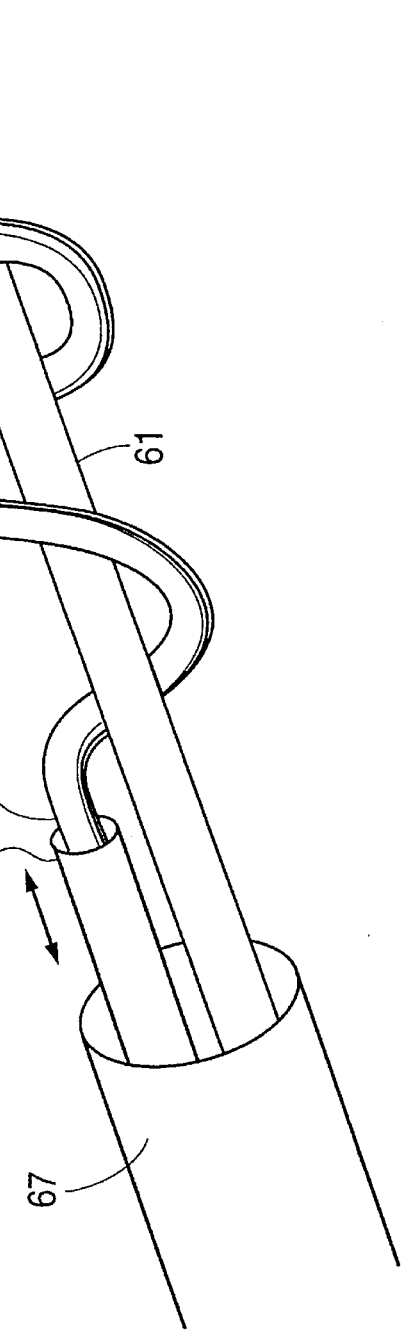

Referring to FIGS. 13A to 13C, an infusion coil and deployment apparatus according to a fifth embodiment of the present invention will be described.

The infusion coil 60 and deployment catheter 61 used in the fifth embodiment are essentially the same as the infusion coil 50 and deployment catheter 51 used in the fourth embodiment. Specifically, the deployment catheter or distal coil holding tube 61 includes a friction lock 62 in the form of an axial bore for securing a distal end 63 of the infusion coil 60 during deployment. A push rod 64 is provided within the distal coil holding tube 61 to release the friction lock 62. In addition, the deployment apparatus includes a proximal holding tube 65 positioned over a linear portion 66 of the infusion coil 60. A containment sheath 67 is disposed over both the proximal and distal holding tubes.

The assembly shown in FIGS. 13A to 13C is particularly useful in instances when a physician desires the ability to position and adjust (compress, elongate, etc.) the infusion coil 60. This is done by first grabbing the distal end 63 of the infusion coil 60 with the friction lock 62, as previously described, and also grabbing the proximal, linear portion 66 of the infusion coil 60 using the proximal holding tube 65. The proximal holding tube 65 is slid over the infusion coil 60 into a position abutting the coiled portion of the infusion coil 60. The proximal holding tube 65 is then clamped or otherwise secured to the infusion coil 60 at the proximal end of the infusion coil 60 outside the containment sheath 67 (at the hub of the deployment apparatus).

In a pre-deployed state of the infusion coil assembly (FIG. 13B), the proximal holding tube 65 and the distal holding tube 61 are slid in opposite directions to elongate the coil 60 and are then pulled into the sheath 67. To deploy the device, the distal holding tube 61 is pushed out of the sheath 67 followed by the proximal holding tube 65 (FIG. 13A). The distal and proximal holding tubes 61, 65 can then be manipulated by the physician to compress and elongate the infusion coil 60 as desired.

Figure 14:
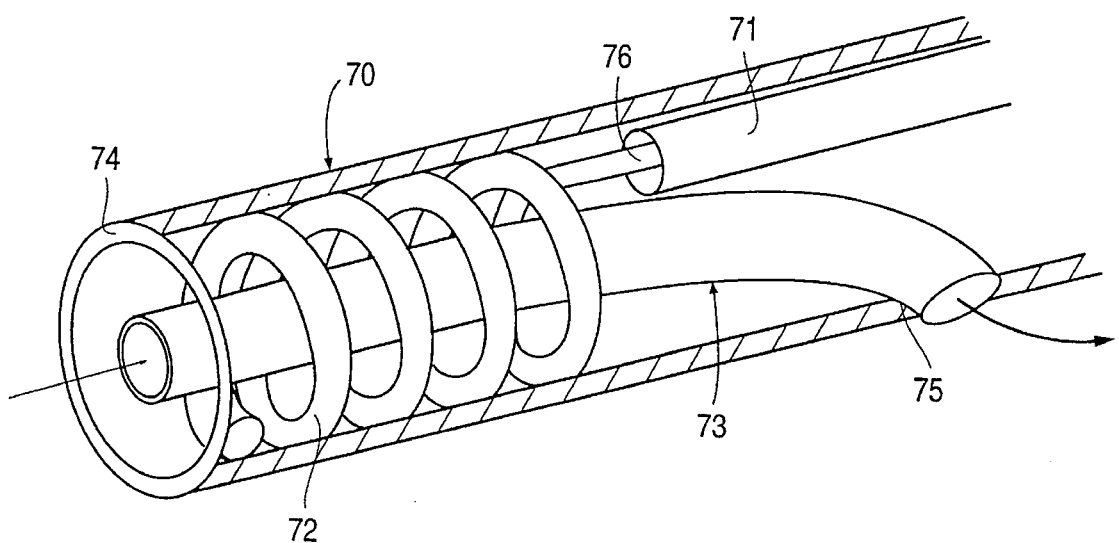
FIG. 14 is a perspective view of a sixth embodiment of the present invention for deploying the infusion coil assembly over a guide wire.

Referring to FIG. 14, a sixth embodiment having a modified deployment assembly for deploying an infusion coil over a guide wire will be described. Guide wires for guiding catheters and deployment devices into a desired location in a vessel of a patient are well known.

As shown in FIG. 14, a modified delivery sheath 70 and push tube 71 are provided for deploying the infusion coil 72 over an existing guide wire (not shown). A guide tube 73 extends from a front opening 74 of the delivery sheath 70 to an opening 75 in a side wall of the delivery sheath 70. The guide tube 73 is permanently secured to the side wall of the delivery sheath 70 by a suitable adhesive or thermal bonding process. The guide tube 73 has an inner diameter large enough to permit the guide wire to pass freely therethrough.

The infusion coil 72 is loaded in the delivery sheath 70 by inserting the linear portion 76 of the infusion coil and push tube 71 into the delivery sheath 70 through the front opening 74. In its loaded position, the coiled portion of the infusion coil 72 is positioned coaxially about the front portion of the guide tube 73. In this manner, the infusion coil 72 can be easily pushed out of the delivery sheath 70 during deployment.

In operation, a proximal end of a guide wire extending outside of a patient is inserted into the front end 77 of the guide tube 73 and pushed through the guide tube 73 until the guide wire exits through the opening 75 in the side wall of the delivery sheath 70. The proximal end of the guide wire is then held by the physician while the loaded delivery sheath 70 and infusion coil assembly are pushed into the vessel of the patient to the desired location using the guide wire for guidance.

The guide tube 73 and modified delivery sheath 70 permit deployment of the infusion coil assembly over an existing guide wire without removing the guide wire and without requiring a guide wire extension to be attached to the guide wire. With the present arrangement, only a short portion of the guide wire must be exposed outside of the patient to permit the delivery sheath 70 to be introduced over the guide wire and into the patient.

By way of example, a 0.016 to 0.018 inch diameter guide wire may be used for a 0.14 inch internal vessel diameter. The guide tube 73 in this example preferably has a 0.020 inch internal diameter (0.022 inch external diameter), and the delivery sheath preferably has a 0.058 inch internal diameter (0.065 inch external diameter).

Figure 15:
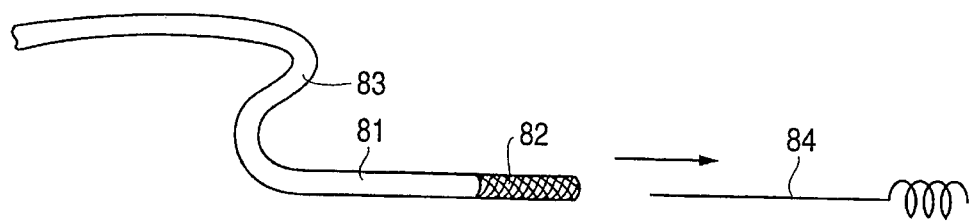
FIG. 15 is an exploded perspective view of an infusion coil showing an alternate construction of the polymer tubing according to the present invention.
Figure 16:
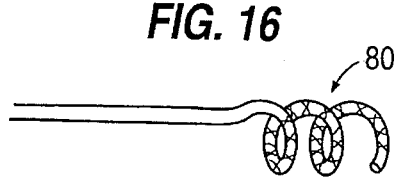
FIG. 16 is an assembled perspective view of the infusion coil shown in FIG. 15.

Referring to FIGS. 15 and 16, an alternate construction of an infusion coil 80 according to the present invention will be described. This alternate construction can be used for any of the coil shapes of the first three embodiments described above, as well as other similar devices.

The polymer tubing 81 of the coil 80 is formed from a braided, stitched or porous tube, such as nylon braids, PVDF porous tubing, or PTFE porous tubing. For a typical catheter construction, the tubing 81 (preform) is cut to approximately 4' to 5' long. The first 95% of the braid/stitch/porous tubing 81 is consolidated by placing the tubing (preform) on a mandrel and heat consolidating the tubing (preform) with a heat shrink, or coating/impregnating the tubing (preform) with a urethane or similar material.

The result of this process, as shown in FIG. 15, is a polymer tubing 81 with a porous or braided end portion 82 and a consolidated (i.e., non-porous) main portion 83. The polymer tubing 81 is then placed over a resilient fiber core 84, as in the previous embodiments. The final result, as shown in FIG. 16, is a soft infusion coil 80 having a porous polymer coating 82 for delivering fluid-based agents about the circumference of the coil.

The soft polymer tubing 81 of the present invention is preferably constructed of a polymer compounded with a radio opacifier at a loading high enough to make it radio-paque. For example, the polymer can be compounded with approximately 75% by weight tungsten. The soft polymer tubing 81 can also be made radiopaque using a suitable coating containing a radio opacifier applied over the polymer tubing.

The distal end of the infusion coil in each of the disclosed embodiments can be sealed or closed in a number of ways according to the present invention. In some applications, particularly where the coiled portion of the polymer tubing is highly porous, it may be unnecessary to close the distal end of the infusion coil. However, in other applications, particularly where a limited number of openings are provided for delivery of fluid-based agents through the polymer tubing, it may be important to close or seal the distal end to prevent the fluid-based agents from flowing out the end of the infusion coil instead of through the delivery openings.

Figure 17A:
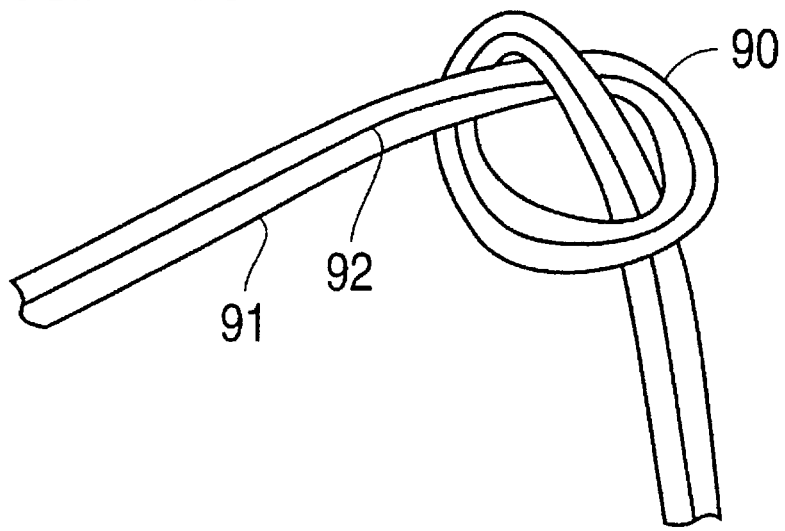
FIGS. 17A to 17C show a series of steps for sealing the distal end of the infusion coil by knotting and thermally consolidating the end of the infusion coil.
Figure 17B:
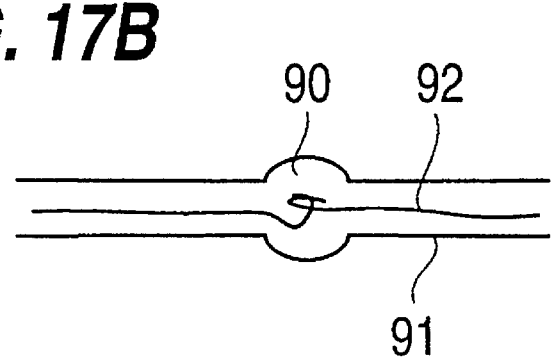
Figure 17C:
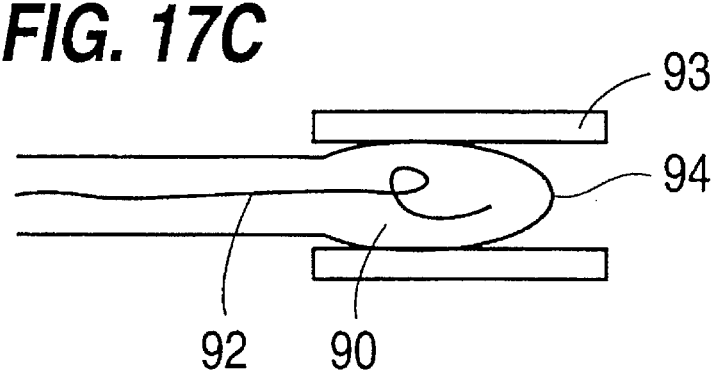

A first way of sealing the distal end of the infusion coil is to knot and consolidate the end of the infusion coil, as shown in FIGS. 17A to 17C. As shown in FIG. 17A, a knot 90 is formed in the end of the infusion coil with both the polymer tubing 91 and the resilient fiber core 92. The knot 90 is then pulled tight, as shown in FIG. 17B, and the excess polymer tubing 91 and resilient fiber core 92 extending past the knot 90 are cut off. The knot 90 is then preferably covered by a short length (e.g., 1–2 mm) of heat shrink tubing 93 (e.g., plastic), as shown in FIG. 17C. The heat shrink tubing 93 is heated and shrunk so that the heat shrink tubing 93 flows over the cut end 94 of the infusion coil and permanently consolidates the knot 90 and heat shrink tubing 93 at the distal end of the infusion coil. As a result, the resilient fiber core 92 is permanently anchored within the polymer tubing 91, and the distal end of the infusion coil is sealed to prevent fluid-based agents from flowing therefrom.

A second way to seal the distal end of the infusion coil is to dip the end of the polymer tubing in a potting agent, such as medical grade silicon, cyanoacrylate, or other suitable adhesive. The potting agent moves into the polymer tubing by capillary action and then cures to form an effective seal and anchor for the resilient fiber core in the end of the infusion coil.

A third way to seal the distal end of the infusion coil is to merely stretch the polymer tubing past the end of the resilient fiber core. Upon stretching a sufficient length, the polymer tubing necks down and permanently sets in such a way as to close the end of the polymer tubing against the flow of fluid-based agents therethrough. The result is a feathered, closed portion of the polymer tubing that extends slightly past the end of the resilient fiber core.

Figure 18:
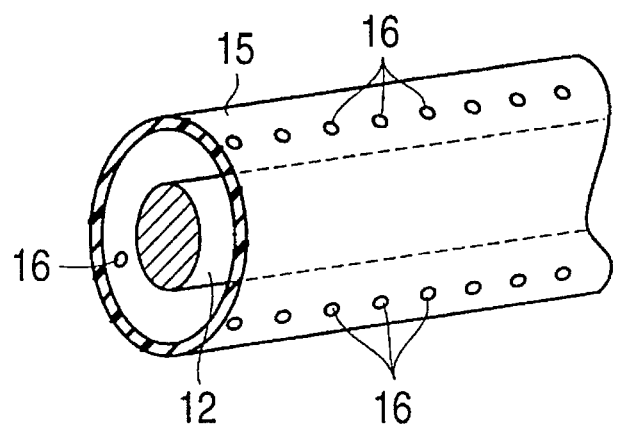
FIG. 18 is an enlarged perspective view of the infusion coil showing a plurality of circumferentially spaced rows of openings for permitting delivery of fluid-based agents through the polymer tubing.

As explained above, holes 16 may be formed in the polymer tubing of the infusion coil by drilling, lasing, machining, punching, and so forth. The holes 16 are preferably formed in the polymer tubing in a plurality of circumferentially spaced rows extending along the length of the coiled portion of the polymer tubing 15. For example, as shown in FIG. 18, three rows of holes 16 can be formed in the polymer tubing 15 with each row of holes 16 being spaced 120 degrees apart from the other rows. The circumferentially spaced rows of holes 16 provide two significant advantages. First, the multiple rows of holes 16 ensure that fluid-based agents will flow about an upstream surface of the coiled portion of the polymer tubing 15 to prevent blood clotting at the point where the blood initially contacts the polymer tubing 15. Second, the multiple rows of holes 16 provide manufacturing convenience in that it is unnecessary to take into account the circumferential location of the holes 16 when forming the coiled portion of the infusion coil.

The disclosed embodiments of the present invention provide an infusion coil that can be wrapped into a much smaller coil without permanently deforming the coil so that it will spring back to its original configuration. The limiting factor of how small a coil can be wound is the thickness of the element to be coiled. For instance, a 0.25" diameter metallic steel heat-tempered spring alloy wire must be wound around a very large radius (several feet) to keep from permanently deforming, while a very thin diameter (e.g., 0.001") spring alloy wire can be wound around a very small radius (0.010") without being permanently set.

Use of "dead" soft polymer tube will follow the coil without hindering recovery of the coil to its original size during deployment. The preferred Shore D hardness of the polymer selected for the polymer tube is approximately 40, whereby any permanent set in the polymer itself due to coiling will not hinder the coil's recovery.

Use of holes or other openings around the entire periphery of the coil prevent thrombus from forming and allows for ease of manufacturing. The size of the resilient fiber core can be tailored to make the springiness of the coil variable so that the device produces a very small force on the vessel wall while still maintaining enough force to recover its coil shape during deployment.

The polymer tube can be tailored to reduce the pressure exerted by the infusion coil on the artery wall. The configuration of the embodiments of the present invention allow for positive and accurate deployment of the infusion coil through existing devices and prevents the infusion coil from dragging through the vessel during deployment. The deployment method permits positive and accurate deployment of the coil through existing devices.

As used in this application, the term "fluid-based agent" encompasses any diagnostic compound, such as dyes for markers, as well as any therapeutic compound that has a desired pharmacologic effect in a particular subject. For example, the fluid-based agent can be an anticoagulant, such as D-Phe-Pro-Arg chloromethyl ketone, an RGD peptide-containing compound, heparin, antithrombin compounds, platelet receptor antagonists, antithrombin antibodies, antiplatelet receptor antibodies, aspirin, protagladin inhibitors, platelet inhibitors, or tick antiplatelet peptide. The fluid-based agent could also be a promoter of vascular cell growth, such as a growth factor promoter, growth factor receptor agonist, transcriptional activator, translational promoter, or endothelia cells. Alternatively, the fluid-based agent can be an inhibitor of vascular cell growth, such as a growth factor inhibitor, growth factor receptor antagonist, transcriptional repressor, translational repressor, antisense DNA, antisense RNA, replication inhibitor, inhibitory antibodies, antibodies directed against growth factors, bifunctional molecules consisting of a growth factor and a cytotoxin, and bifunctional molecules consisting of an antibody and a cytotoxin. In addition, the fluid-based agent could be a cholesterol-lowering agent, a vasodilating agent, and agents that interfere with endogenous vasoactive mechanisms.

While the present invention has been disclosed primarily in connection with treating coronary artery disease, the invention may also be used for treatment of various other body organs, including the biliary ducts, or the genital-uretal organs. The term vessel, as used in this application, encompasses any duct, canal, or other tube that contains or conveys a body fluid.

It will be appreciated that the present invention is not limited to the exact construction or method steps that have been described above and illustrated in the accompanying drawings, and that various modifications and changes can be made without departing from the scope of the invention. It is intended that the scope of the invention only be limited by the appended claims.

We claim:

1. An infusion coil apparatus for delivering fluid-based agents intravascularly, comprising:

a resilient fiber core having a linear portion and a coiled portion; and a polymer tubing encasing the resilient fiber core and adapting to the shape of the resilient fiber core, said polymer tubing comprising a first portion encasing the linear portion of the resilient fiber core and a second portion encasing the coiled portion of the resilient fiber core.

2. The infusion coil apparatus according to claim 1, wherein said polymer tubing has a lumen extending along a length of said polymer tubing, and said second portion of the polymer tubing comprises means for releasing fluid-based agents delivered through said lumen from the infusion coil apparatus.

3. The infusion coil apparatus according to claim 2, wherein said releasing means comprises a series of openings spaced along said second portion of the polymer tubing, said series of openings being spaced along a circumference of a coil shape of the infusion coil apparatus.

4. The infusion coil apparatus according to claim 3, wherein said openings are formed in a plurality of circumferentially spaced rows extending along a length of the second portion of the polymer tubing.

5. The infusion coil apparatus according to claim 1, wherein said second portion of the polymer tubing is constructed of a porous material for releasing fluid-based agents from said infusion coil apparatus.

6. The infusion coil apparatus according to claim 1, wherein said second portion of the polymer tubing is constructed of a braided or stitched material for releasing fluid-based agents from said infusion coil apparatus.

7. The infusion coil apparatus according to claim 1, wherein said resilient fiber core has a diameter of 0.002 to 0.006 inches.

8. The infusion coil apparatus according to claim 7, wherein said polymer tubing has an outside diameter of 0.012 to 0.014 inches and an inside diameter of 0.006 to 0.008 inches.

9. The infusion coil apparatus according to claim 1, wherein said polymer tubing is formed of a very soft material selected from the group consisting of nylon, urethane, PE and TFE polymer materials so as to minimize resistance to the coiled portion of the resilient fiber core and prevent damage to a vessel during use.

10. The infusion coil apparatus according to claim 1, wherein said polymer tubing is formed of a polymer having a Shore D hardness of approximately 40.

11. The infusion coil apparatus according to claim 1, wherein said polymer tubing is constructed of a polymer compounded with a radio opacifier at a loading high enough to make the polymer radiopaque.

12. The infusion coil apparatus according to claim 11, wherein said polymer of said polymer tubing is compounded with approximately 75% by weight tungsten.

13. The infusion coil apparatus according to claim 1, wherein said resilient fiber core extends through a lumen of said polymer tubing, and said second portion of the polymer tubing comprises means for releasing fluid-based agents delivered through said lumen from the infusion coil apparatus.

14. The infusion coil apparatus according to claim 1, wherein said coiled portion of said resilient fiber core is shaped into a forward feed coil shape extending away from said linear portion of said resilient fiber core.

15. The infusion coil apparatus according to claim 1, wherein said resilient fiber core is shaped into a reverse feed coil shape with a bent transition portion between said linear portion and said coiled portion, said bent transition portion directing said coiled portion in a reverse direction back along said linear portion.

16. The infusion coil apparatus according to claim 1, wherein said resilient fiber core is formed of a metallic steel heat-tempered spring alloy.

17. The infusion coil apparatus according to claim 1, wherein said resilient fiber core is formed of a resilient boron fiber.

18. The infusion coil apparatus according to claim 1, wherein a distal end portion of the coiled portion of the resilient fiber core and the second portion of the polymer tubing are knotted and thermally consolidated to anchor the resilient fiber core within the polymer tubing and seal the distal end portion of the polymer tubing.

19. The infusion coil apparatus according to claim 1, wherein a distal end portion of the resilient fiber core is potted with a curable potting agent to anchor the resilient fiber core within the polymer tubing and seal the distal end portion of the polymer tubing.

20. In combination, an infusion coil apparatus for delivering fluid-based agents intravascularly and an apparatus for deploying the infusion coil apparatus at a desired location in a vessel, said infusion coil apparatus comprising:

a resilient fiber core having a linear portion and a coiled portion; and a polymer tubing encasing the resilient fiber core and adapting to the shape of the resilient fiber core, said polymer tubing comprising a first portion encasing the linear portion of the resilient fiber core and a second portion encasing the coiled portion of the resilient fiber core.

21. The combination according to claim 20, wherein said apparatus for deploying the infusion coil apparatus comprises a delivery sheath, said delivery sheath having an inside diameter that is smaller than a preset diameter of said coiled portion for compressing the infusion coil apparatus during deployment.

22. The combination according to claim 21, wherein said apparatus for deploying the infusion coil apparatus further comprises a push tube for pushing the infusion coil apparatus out of said delivery sheath during deployment, said push tube being slidable over a linear portion of the infusion coil apparatus.

23. The combination according to claim 21, wherein said resilient fiber core is shaped into a reverse feed coil shape with a bent transition portion between said linear portion and said coiled portion, said bent transition portion directing said coiled portion in a reverse direction back along said linear portion.

24. The combination according to claim 23, wherein said apparatus for deploying the infusion coil apparatus further comprises a deployment catheter that is slidable over the infusion coil apparatus, said deployment catheter comprising a slotted distal end for receiving said bent transition portion of the infusion coil apparatus to permit pushing and twisting of the infusion coil apparatus during deployment.

25. The combination according to claim 24, further comprising a first marker at a forward distal end of said deployment catheter and a second marker spaced axially rearwardly from said first marker, said first and second markers being radiopaque for determining placement of the infusion coil apparatus within a vessel.

26. The combination according to claim 25, wherein said first and second markers are spaced apart a distance equal to an axial length of said coiled portion in a relaxed position of said coiled portion.

27. The combination according to claim 26, wherein said polymer tubing is constructed of a polymer compounded with a radio opacifier at a loading high enough to make the polymer radiopaque.

28. The combination according to claim 21, wherein said coiled portion of said resilient fiber core is shaped into a forward feed coil shape extending away from said linear portion of said resilient fiber core and includes a distal end portion.

29. The combination according to claim 28, wherein said apparatus for deploying the infusion coil apparatus further comprises a deployment catheter having a means for holding said distal end portion to permit pushing and twisting of the infusion coil apparatus during deployment.

30. The combination according to claim 29, wherein said holding means comprises a notch in a distal end of the deployment catheter for receiving said distal end portion of the infusion coil apparatus.

31. The combination according to claim 29, further comprising a first marker at a forward distal end of said deployment catheter and a second marker spaced axially rearwardly from said first marker, said first and second markers being radiopaque for determining placement of the infusion coil apparatus within a vessel.

32. The combination according to claim 31, wherein said first and second markers are spaced apart a distance equal to an axial length of said coiled portion in a relaxed position of said coiled portion.

33. The combination according to claim 32, wherein said polymer tubing is constructed of a polymer compounded with a radio opacifier at a loading high enough to make the polymer radiopaque.

34. The combination according to claim 29, wherein said holding means comprises a friction lock formed in a distal end of said deployment catheter.

35. The combination according to claim 34, wherein said friction lock comprises an axially extending bore in the distal end of said deployment catheter into which the distal end portion of the infusion coil is inserted.

36. The combination according to claim 35, further comprising a push rod slidably disposed within said deployment catheter for releasing said friction lock.

37. The combination according to claim 35, wherein said friction lock further comprises a notch formed in a side wall of said deployment catheter for engaging the infusion coil and facilitating twisting of the infusion coil during deployment.

38. The combination according to claim 29, further comprising a proximal holding tube positioned over a linear portion of the infusion coil, said proximal holding tube having a distal end abutting a coiled portion of the infusion coil, said proximal holding tube being secured to the infusion coil to permit manipulation of said infusion coil during deployment using said proximal holding tube in conjunction with said deployment catheter.

39. The combination according to claim 21, further comprising a guide tube extending from a point adjacent a distal end of the delivery sheath to an opening in a side wall of the delivery sheath, said guide tube being secured to the side wall of the delivery sheath and having an inner diameter large enough to permit a guide wire to pass therethrough.

40. A method for delivering fluid-based agents into a vessel, comprising the steps of:

providing an infusion coil apparatus having a resilient fiber core encased by a soft polymer tubing;

loading said infusion coil apparatus into a delivery sheath, said delivery sheath having an internal diameter which is smaller than a preset diameter of a coiled portion of said resilient fiber core;

inserting said delivery sheath and said infusion coil apparatus into a vessel; and pushing said infusion coil apparatus out of said delivery sheath whereby said resilient fiber core causes said infusion coil apparatus to increase in diameter and lodge in the vessel.

41. The method for delivering fluid-based agents into a vessel according to claim 40, further comprising the step of feeding a fluid-based agent through said polymer tubing of said infusion coil apparatus into said vessel.

42. The method for delivering fluid-based agents into a vessel according to claim 40, further comprising the steps of sliding a push tube over a linear portion of said infusion coil apparatus, and pushing said infusion coil apparatus out of said delivery sheath using said push tube.

43. The method for delivering fluid-based agents into a vessel according to claim 42, further comprising the step of removing said push tube and said delivery sheath from said vessel while maintaining said infusion coil apparatus within said vessel.

44. The method for delivering fluid-based agents into a vessel according to claim 43, further comprising the step of removing said infusion coil apparatus from said vessel by pulling an exposed end of said infusion coil apparatus.

45. The method for delivering fluid-based agents into a vessel according to claim 42, further comprising the steps of:

providing a guide tube within said delivery sheath, said guide tube having a first distal end adjacent to a distal end of said delivery sheath and a second proximal end in communication with an opening through a side wall of said delivery sheath; and sliding the guide tube over a guide wire to facilitate the step of inserting said delivery sheath and said infusion coil apparatus into a vessel.

46. The method for delivering fluid-based agents into a vessel according to claim 40, further comprising the steps of:

providing said infusion coil apparatus with a reverse feed coil shape with a bent transition portion between a linear portion and a coiled portion, said bent transition portion directing said coiled portion in a reverse direction back along said linear portion;

providing a deployment catheter having a slotted distal end;

sliding said deployment catheter over the infusion coil apparatus and receiving the bent transition portion of the infusion coil apparatus in the slotted distal end of the deployment catheter;

pushing the infusion coil apparatus out of the delivery sheath into the vessel with said deployment catheter; and twisting said deployment catheter to rewind the infusion coil apparatus into a deployed position against a wall of the vessel.

47. The method for delivering fluid-based agents into a vessel according to claim 46, further comprising the steps of:

providing first and second radiopaque marks on said deployment catheter, said first and second marks being spaced apart a distance approximately equal to an axial length of said coiled portion in a relaxed position of the infusion coil apparatus; and twisting said deployment catheter to rewind said infusion coil apparatus until the axial length of said coiled portion is approximately the same as the distance between said first and second marks.

48. The method for delivering fluid-based agents into a vessel according to claim 40, further comprising the steps of:

providing said infusion coil apparatus with a forward feed coil shape extending away from a linear portion of said resilient fiber core, and a distal end portion;

providing a deployment catheter having a holding structure in a distal end of the deployment catheter;

receiving and securing said distal end portion of the infusion coil apparatus in said holding structure of the deployment catheter;

pushing the infusion coil apparatus out of the delivery sheath into the vessel with said deployment catheter; and twisting said deployment catheter to rewind the infusion coil apparatus into a deployed position against a wall of the vessel.

49. The method for delivering fluid-based agents into a vessel according to claim 48, further comprising the steps of:

providing first and second radiopaque marks on said deployment catheter, said first and second marks being spaced apart a distance approximately equal to an axial length of said coiled portion in a relaxed position of the infusion coil apparatus; and twisting said deployment catheter to rewind said infusion coil apparatus until the axial length of said coiled portion is approximately the same as the distance between said first and second marks.

50. The method for delivering fluid-based agents into a vessel according to claim 40, further comprising the steps of:

providing said infusion coil apparatus with a forward feed coil shape extending away from a linear portion of said resilient fiber core, and a distal end portion;

providing a deployment catheter having a holding structure in a distal end of the deployment catheter;

receiving and securing said distal end portion of the infusion coil apparatus in said holding structure of the deployment catheter;

providing a proximal holding tube over a linear portion of the infusion coil, said proximal holding tube having a distal end abutting a coiled portion of the infusion coil, said proximal holding tube being secured to the infusion coil;

sliding the proximal holding tube and the deployment catheter in opposite directions to elongate and reduce the diameter of a coiled portion of the infusion coil apparatus;

placing the elongated coil into said delivery sheath;

pushing the infusion coil apparatus out of the delivery sheath into the vessel using said deployment catheter and said proximal holding tube; and sliding the proximal holding tube and the deployment catheter in opposite directions to compress and increase the diameter of the coiled portion of the infusion coil apparatus, whereby the infusion coil apparatus is placed in a deployed position against a wall of the vessel.

51. The combination according to claim 20, wherein said polymer tubing is constructed of a polymer compounded with a radio opacifier at a loading high enough to make the polymer radiopaque.

52. The method for delivering fluid-based agents into a vessel according to claim 40, further comprising the steps of:

encasing the resilient fiber core with a soft polymer tubing formed of a polymer compounded with a radio opacifier at a loading high enough to make the polymer radiopaque; and observing the infusion coil apparatus during deployment into a vessel using an X-ray device.

\* \* \* \* \*